(12) United States Patent
Opperman (10) Patent No.: US 11,432,716 B2
(45) Date of Patent: *Sep. 6, 2022

(54) RETRACTOR AND TIP EXTENDER THEREFOR

(71) Applicant: Colorado Voice Clinic, P.C., Denver, CO (US)

(72) Inventor: David A. Opperman, Littleton, CO (US)

(73) Assignee: Colorado Voice Clinic, P.C., Denver, CO (US)

( * ) Notice: Subject to any disclaimer, the term of this patent is extended or adjusted under 35 U.S.C. 154(b) by 563 days.

This patent is subject to a terminal disclaimer.

(21) Appl. No.: 16/511,565

(22) Filed: Jul. 15, 2019

(65) Prior Publication Data

US 2020/0375446 A1 Dec. 3, 2020

Related U.S. Application Data

(63) Continuation of application No. 16/169,789, filed on Oct. 24, 2018, now Pat. No. 10,349,823, which is a continuation-in-part of application No. 15/457,404, filed on Mar. 13, 2017, now Pat. No. 10,238,373.

(60) Provisional application No. 62/593,551, filed on Dec. 1, 2017.

(51) Int. Cl.
*A61B 1/267* (2006.01)
*A61B 1/00* (2006.01)

(52) U.S. Cl.
CPC .......... *A61B 1/267* (2013.01); *A61B 1/00089* (2013.01); *A61B 1/00101* (2013.01)

(58) Field of Classification Search
CPC .............................. A61B 1/267; A61B 1/2673

USPC .................................................. 600/185–199
See application file for complete search history.

(56) References Cited

U.S. PATENT DOCUMENTS

| | | | |
|---|---|---|---|
| 2,070,820 | A | 2/1937 | Allyn |
| 2,131,372 | A | 9/1938 | Flood |
| 2,152,349 | A | 3/1939 | Flood |
| D168,363 | S | 12/1952 | Martin |
| 3,426,749 | A | 2/1969 | Jephcott |
| D220,855 | S | 6/1971 | Montague |
| 4,114,609 | A | 9/1978 | Moses |

(Continued)

FOREIGN PATENT DOCUMENTS

| | | |
|---|---|---|
| WO | 199014041 A1 | 11/1990 |
| WO | 2013177540 A1 | 11/2013 |

(Continued)

OTHER PUBLICATIONS

Olympus FK-WO TORS Laryngo-pharyngoscope retractor. http://olympusmedical.com.sg/products/all-products/ instruments/ent-instruments/fk-wo-tors-laryngo-pharyngoscope-retractor/index.html. Retrieved from the internet Mar. 2016. 3 pages.

(Continued)

*Primary Examiner* — Eric S Gibson
(74) *Attorney, Agent, or Firm* — FisherBroyles, LLP; Craig W. Mueller (57) ABSTRACT

A retractor used in inner-oral surgery is provided that includes a maxilla portion configured to maintain a patient's mount in an open state. The retractor also includes a blade that maintains the position of the tongue so that surgical tools are not obstructed. The maxilla portion of one embodiment only extends a portion of the length of the blade.

17 Claims, 11 Drawing Sheets

(56) References Cited

U.S. PATENT DOCUMENTS

| | | | |
|---|---|---|---|
| 4,306,547 A * | 12/1981 | Lowell | A61B 1/07 128/200.26 |
| 4,384,570 A | 5/1983 | Roberts | |
| D270,183 S | 8/1983 | Govenius | |
| 4,579,108 A | 4/1986 | Bauman | |
| 4,832,020 A * | 5/1989 | Augustine | A61M 16/0495 128/207.14 |
| 4,982,729 A * | 1/1991 | Wu | A61B 1/267 600/187 |
| 5,065,738 A * | 11/1991 | Van Dam | A61B 1/00142 600/185 |
| 5,092,314 A * | 3/1992 | Zeitels | A61B 1/267 600/194 |
| D338,240 S | 8/1993 | Mori | |
| D338,688 S | 8/1993 | Mori | |
| 5,261,392 A * | 11/1993 | Wu | A61B 1/07 600/187 |
| 5,776,053 A * | 7/1998 | Dragisic | A61B 1/267 600/195 |
| 5,893,830 A * | 4/1999 | Zeitels | A61B 1/267 600/185 |
| D438,979 S | 3/2001 | Gomes | |
| 6,652,453 B2 * | 11/2003 | Smith | A61B 1/015 600/188 |
| D486,908 S | 2/2004 | Himbert | |
| 6,955,645 B1 * | 10/2005 | Zeitels | A61B 1/24 600/187 |
| D540,945 S | 4/2007 | Darnold | |
| D558,347 S | 12/2007 | Darnold | |
| D629,897 S | 12/2010 | Koros | |
| 7,946,981 B1 * | 5/2011 | Cubb | A61B 1/00103 600/187 |
| D685,087 S | 6/2013 | Voic | |
| 8,495,999 B2 * | 7/2013 | Law | A61B 1/0684 128/200.26 |
| 8,721,535 B2 * | 5/2014 | Chen | A61M 16/0495 600/188 |
| D742,512 S | 11/2015 | Pilz | |
| D779,665 S | 2/2017 | Hasbun | |
| 10,238,373 B1 * | 3/2019 | Opperman | A61B 1/24 |
| 10,349,823 B2 * | 7/2019 | Opperman | A61B 1/267 |
| D866,759 S | 11/2019 | Opperman | |
| D868,249 S | 11/2019 | Chen | |
| D877,330 S | 3/2020 | McClunan | |
| D877,331 S | 3/2020 | Huels | |
| 2005/0054972 A1 | 3/2005 | Adams | |
| 2006/0276693 A1 * | 12/2006 | Pacey | A61B 1/31 600/188 |
| 2009/0318768 A1 * | 12/2009 | Tenger | A61M 16/0495 600/194 |
| 2010/0298644 A1 * | 11/2010 | Kleene | A61B 1/2676 128/207.14 |
| 2011/0178372 A1 * | 7/2011 | Pacey | A61B 1/00142 600/188 |
| 2011/0306839 A1 * | 12/2011 | Young | A61B 1/267 600/188 |
| 2012/0095295 A1 * | 4/2012 | McGrath | A61M 16/0488 600/194 |
| 2013/0237763 A1 * | 9/2013 | Qiu | A61M 16/0488 600/188 |
| 2013/0310650 A1 * | 11/2013 | Hales | A61B 1/267 600/196 |
| 2014/0336466 A1 * | 11/2014 | Young | A61B 1/00142 600/188 |
| 2015/0173598 A1 * | 6/2015 | Alexander | A61B 1/015 600/187 |
| 2016/0354072 A1 | 12/2016 | Swift | |
| 2017/0189004 A1 | 7/2017 | Swift | |
| 2018/0021100 A1 | 1/2018 | Swift | |
| 2018/0110403 A1 | 4/2018 | Okazaki | |
| 2018/0110503 A1 | 4/2018 | Flock | |
| 2019/0076138 A1 * | 3/2019 | Opperman | A61B 1/00101 |
| 2019/0082947 A1 * | 3/2019 | Opperman | A61B 1/24 |
| 2020/0375446 A1 * | 12/2020 | Opperman | A61B 1/00089 |

FOREIGN PATENT DOCUMENTS

| | | |
|---|---|---|
| WO | 2015136518 A1 | 9/2015 |
| WO | WO-2019108960 A1 | 6/2019 |

OTHER PUBLICATIONS

International Search Report and Written Opinion of related PCT Application No. PCT/US2018/063353. dated Jan. 18, 2019. 7 pages.

Extended European Search Report from related EP18883847. dated Nov. 5, 2021. 11 Pages.

* cited by examiner

RETRACTOR AND TIP EXTENDER THEREFOR

This application is a continuation of U.S. patent application Ser. No. 16/169,789, filed Oct. 24, 2018, now U.S. Pat. No. 10,349,823, issued Jul. 16, 2019, which is a continuation-in-part of U.S. patent application Ser. No. 15/457,404, filed Mar. 13, 2017, now U.S. Pat. No. 10,238,373, issued Mar. 26, 2019, which claims the benefit of U.S. Provisional Patent Application Ser. No. 62/307,333, filed Mar. 11, 2016, the entire disclosures of which are incorporated by reference herein.

This application also claims the benefit of U.S. Provisional Patent Application Ser. No. 62/593,551, filed Dec. 1, 2017, the entire disclosure of which is incorporated by reference herein.

FIELD OF THE INVENTION

Embodiments of the present invention are generally related to a robotic access retractor for oral cavity, oropharynx, hypopharynx, and larynx procedures. More specifically, one embodiment of the present invention is a retractor supported by a gallows laryngoscope holder that facilitates the use of traditional or robotic medical instruments. The retractor of one embodiment of the present invention possesses, or receives, a curved tip that facilitates lifting a patient's epiglottis for enhanced visualization of the laryngeal introitus.

BACKGROUND OF THE INVENTION

Laryngoscopes are routinely used to facilitate endotracheal intubation of patients, to provide an air passage for administration of anesthesia, and/or to establish an airway. In addition, laryngoscopes are commonly used in surgery to displace pharyngeal tissues to permit direct inspection of the larynx (i.e. direct laryngoscopy). Many laryngoscopes are L-shaped having a handle connected to a curved or straight blade. Otolaryngologists typically use a tube-shaped laryngoscope to view the larynx and operate endoscopically on the true vocal cords (i.e. glottis). U.S. Pat. Nos. 4,384,570 and 5,092,314, which are incorporated by reference herein, discuss common laryngoscopes.

Laryngoscopes are often used with gallows-type holders that suspend a tubular retractor that accomodates traditional or robotic surgical instruments. The gallows holder and retractor support the patient's head and provides a clear path for traditional or robotic instruments to reach the larynx.

Alternatively, laryngoscopes are used, albeit less effectively, with jaw spreaders where mouth and larynx tissue are moved by various retractors interconnected to a peripheral structure positioned about the patient's head. One of the retractors interconnected to the peripheral structure is a non-cylindrical blade designed to hold the tongue in an ideal location. One drawback of using jaw spreaders, for example, those manufactured by Olympus® under the trade name FK-WO TORS, is that the retractors used are ineffective for endolaryngial surgery.

Thus, there is a long-felt need to provide a retractor for endolarynginal surgeries that effectively moves and maintains pharyngeal, epiglottal, and endolaryngeal tissue so the traditional or robotic surgical instruments (linear or flexible) can be used.

SUMMARY OF THE INVENTION

It is one aspect of embodiments of the present invention to provide a retractor for use with laryngoscopes. The contemplated retractor can accommodate traditional or robotic medical instruments. More specifically, some embodiments of the present invention comprise a tool that allows a robot to access a surgical site through a patient's mouth, oropharynx, pharynx, hypopharynx, and larynx.

It is another aspect of embodiments of the present invention to provide a retractor with a maxilla portion for contact with a patient's upper teeth that is shorter than a blade configured to retract the patient's tongue. A portion of the blade may be considered a mandibular portion that engages the patient's lower teeth. The maxilla portion, mandibular portion, and the blade are curved in such a way to provide a generally cylindrical passage for the receipt of traditional or robotic medical instruments.

Common laryngoscopes and the laryngoscopes described herein, have a tip configuration designed to be placed near the epiglottic vallecula (i.e., the depression behind the root of a patient's tongue behind the folds of the throat) to retract the patient's tongue and to expose the esophagus, bottom of the tongue, and posterior larynx. It is another aspect of some embodiments of the present invention to provide an extended tip that increases the degree of lift, which enhances access to patient anatomy. More specifically, a tip extender may be provided that selectively interconnects to the tip of a laryngoscope blade as described herein or to any one of the laryngoscope blades being currently used. The extended tip of the laryngoscope blade can be placed closer to the epiglottic petiole so that the epiglottis and anterior commisure (i.e., the attachment of the true vocal folds to thyroid cartilage) are also retracted to provide a clear view of the false vocal folds, true vocal folds, and glottis. As those of ordinary skill in the art will appreciate, this functionality may serve as a gateway to the patient's trachea and lungs. The contemplated retractor blade and tip elevates pharyngeal and laryngeal tissue and tilts the epiglottis to create enhanced exposure deep inside the pharynx, larynx, and trachea. Thus, the tip extender provides exposure to an operative field that a flexible or curved robot can navigate and deliver instrumentation directly to an area of interest.

It is another aspect of embodiments of the present invention to provide a retractor adapted for use with a laryngoscope, comprising: a blade having a proximal end and a distal end; a maxilla portion interconnected to the blade, wherein the maxilla portion and the blade are curved about a longitudinal axis of the retractor that generally corresponds to the length of the blade to provide at least a portion of a passage adapted to selectively receive a medical instrument; and wherein the maxilla portion has proximal end and a distal end that define a length that is less than or equal to 75% of the length of the blade.

It is still yet another aspect of some embodiments of the present invention to provide a retractor, comprising: a first member having a proximal end and a distal end; a second member interconnected to the first member, wherein at least one of the first member and the second member are curved about a longitudinal axis of the retractor that generally corresponds to the length of the first member to provide a passage; and wherein the second portion has a length that is substantially less than that of the first portion.

It is still yet another aspect of some embodiments of the present invention to provide a retractor adapted for use with a laryngoscope, comprising: a blade having a proximal end and a distal end; a maxilla portion interconnected to the blade, wherein the maxilla portion and the blade are curved about a longitudinal axis of the retractor that generally corresponds to the length of the blade to provide a passage configured to selectively receive a medical instrument;

wherein the maxilla portion has proximal end and a distal end that define a length that is substantially less than the length of the blade; wherein the distal end of the blade has a tapered shape; wherein the maxilla portion has a first lateral edge and a second lateral edge interconnected to corresponding lateral edges of the blade, the maxilla portion also comprising a shaped surface that extends from the first lateral edge to the second lateral edge, and wherein the shaped surface includes an outer portion that has a longitudinal dimension greater than the length of the first lateral edge and the second lateral edge; wherein the proximal end of the maxilla portion provides a lateral opening in the retractor; and wherein the distal end of the blade is spaced from the longitudinal axis of the retractor.

The Summary of the Invention is neither intended nor should it be construed as being representative of the full extent and scope of the present invention. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

The following component list and associated numbering found in the drawings is provided to assist in the understanding of one embodiment of the present invention:

| # | Component |
|---|---|
| 2 | Retractor |
| 6 | Blade |
| 10 | Handle |
| 14 | Mouth |
| 18 | Tip |
| 22 | Vallecula |
| 26 | Patient |
| 30 | Tongue |
| 32 | Soft Palate |
| 34 | Lower lip |
| 38 | Tongue |
| 40 | Pharynx |
| 42 | Larynx |
| 46 | Maxilla portion |
| 50 | Mandibular portion |
| 54 | Teeth |
| 58 | Upper lip |
| 62 | Opening |
| 66 | Passage |
| 70 | Epiglottis |
| 74 | Vocal folds |
| 78 | Side opening |
| 82 | Taper |
| 86 | Tip extender |
| 90 | Leg |
| 94 | Rail |
| 98 | End |
| 102 | Lateral Surface |
| 106 | Groove |
| 110 | Epiglottic petiole |
| 114 | Track |
| 118 | Lateral edge |
| 122 | Floor |
| 126 | Cavity |

It should be understood that the drawings are not necessarily to scale. In certain instances, details not necessary for an understanding of the invention or that render other details difficult to perceive may have been omitted. It should be understood, of course, that the invention is not necessarily limited to the particular embodiments illustrated herein.

DETAILED DESCRIPTION

FIGS. 1-8 show the retractor 2 of one embodiment of the present invention that includes a blade 6 interconnected to a handle 10 which selectively interfaces with a gallows support. The blade is configured to be placed in a patient's mouth 14, wherein a blade tip 18 is placed into the patient's valleculla 22. Because the patient 26 is lying on their back, the blade 6 serves to prevent the tongue 34, lower lip 36 and tissue of the pharynx 40 and larynx 42 from blocking the oral cavity. The blade 6 is curved about its longitudinal axis (A) to provide a semi-cylindrical profile that generally contours the patient's physiology. The blade contour also serves to raise the blade tip 18 so it can better interface with the valleculla 22. The blade 6 is also curved at the tip at an angle ($\Theta$) relative to the longitudinal axis of the retractor. The retractor includes a maxilla portion 46 and mandibular portion 50 configured to maintain a patient's mouth open by interfacing with their teeth 54 and upper lip 58 and lower lip 34. The maxilla portion 46 is generally cylindrical, thereby providing an opening 62 and a passage 66 that receives and accommodates robotic or traditional surgical instruments. One of ordinary skill in the art will appreciate the maxilla and/or mandibular portions may possess a faceted outer profile and not have smooth surfaces as shown.

As shown in FIGS. 1, 2, 7 and 8, the maxilla portion of one embodiment of the present invention does not extend to a point adjacent to the blade tip 18. In contrast, prior art tools used in manual, or in some robotic, surgeries require line-of-sight and, thus, possess an elongated maxilla portion to support oral cavity tissue. As will be appreciated by one of ordinary skill in the art, before the advent of modern articulating, curved, or flexiblesurgical tools, there was no motivation to extend surgical tool length to accommodate surgeries posterior to the epiglottic valleculla 22. Indeed, extending prior art tools to engage and hold the epiglottis 70 would provide the surgeon an inferior line-of-sight to the patient's vocal folds 74 (i.e., vocal cords). The extended tubular nature of the prior art maxilla/mandibular portions coupled with the angle of insertion required by rigid or straight prior art tools would locate the end of the tool closer to the rear portion of the patient's throat. Surgeons using prior art manual and some rigid robotic tools would have to apply force to the patient's head to address this drawback and expose areas of interest. Prior art manual and straight/rigid robotic surgical tools simply do not have the capability to comfortably accommodate patient physiology in a way that provides a surgeon the maximum operative options. Modern surgical tools, which have curved or flexible portions do not require the level of tissue support previously needed. In addition, use of an elongated tube may adversely affect the functionality of a flexible robotic tool by limiting degrees of freedom. Further, newer robotic surgical tools, which do not require line-of-sight and which can articulate, flex, and bend, do not suffer drawbacks of the prior art, including the need to force the patient's head to gain visual access to the surgical sight. Accordingly, in some embodiments of the present invention the length of the maxilla portion ($L_2$) is less than half the length of the blade ($L_1$), which provides a surgeon using flexible robotic instruments and systems enhanced access to a multitude of previously-unattainable areas of the patient's larynx 42.

Figure 1:
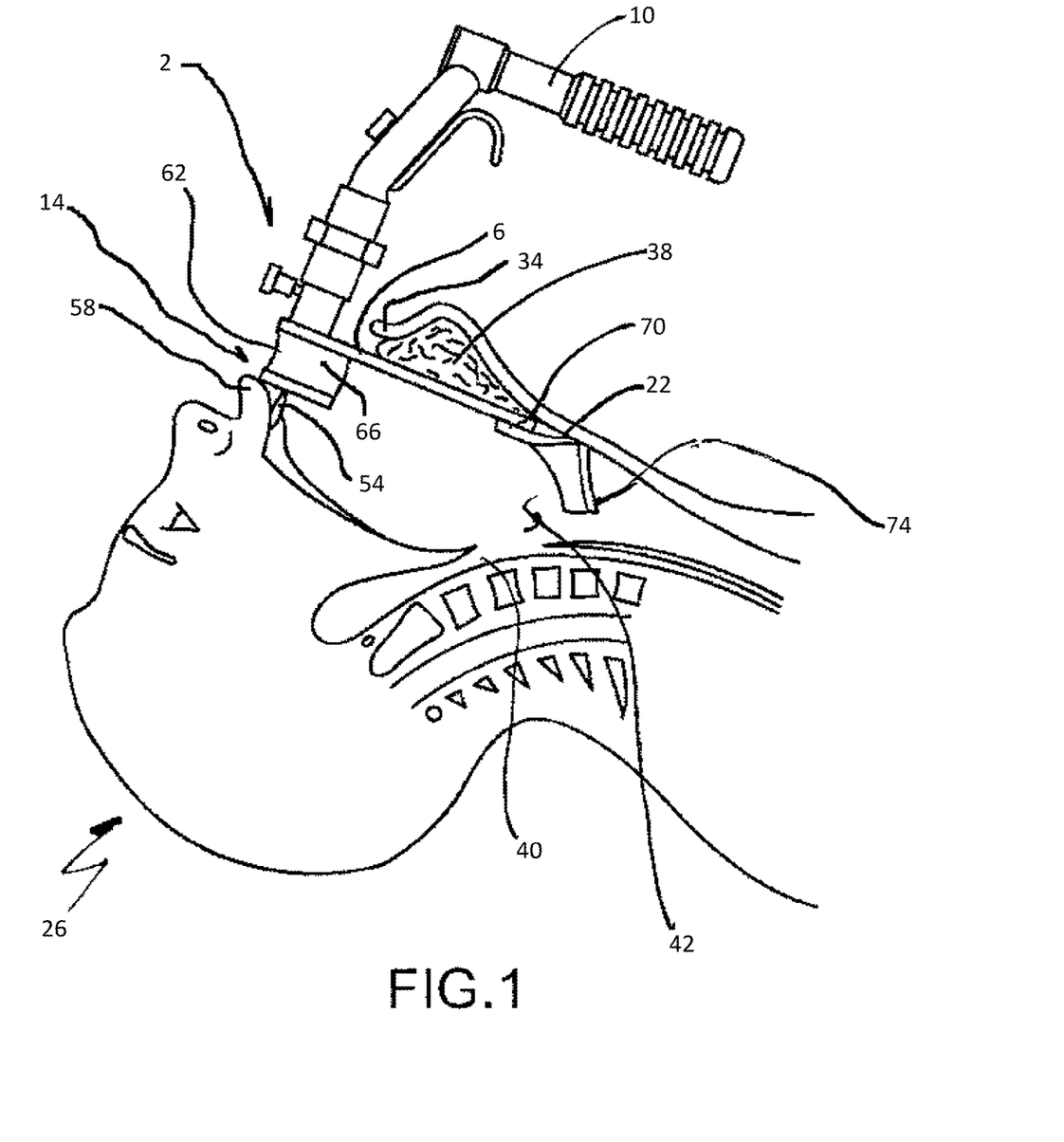
FIG. 1 is an elevation view of a retractor of one embodiment of the present invention positioned in a patient's mouth.
Figure 2:
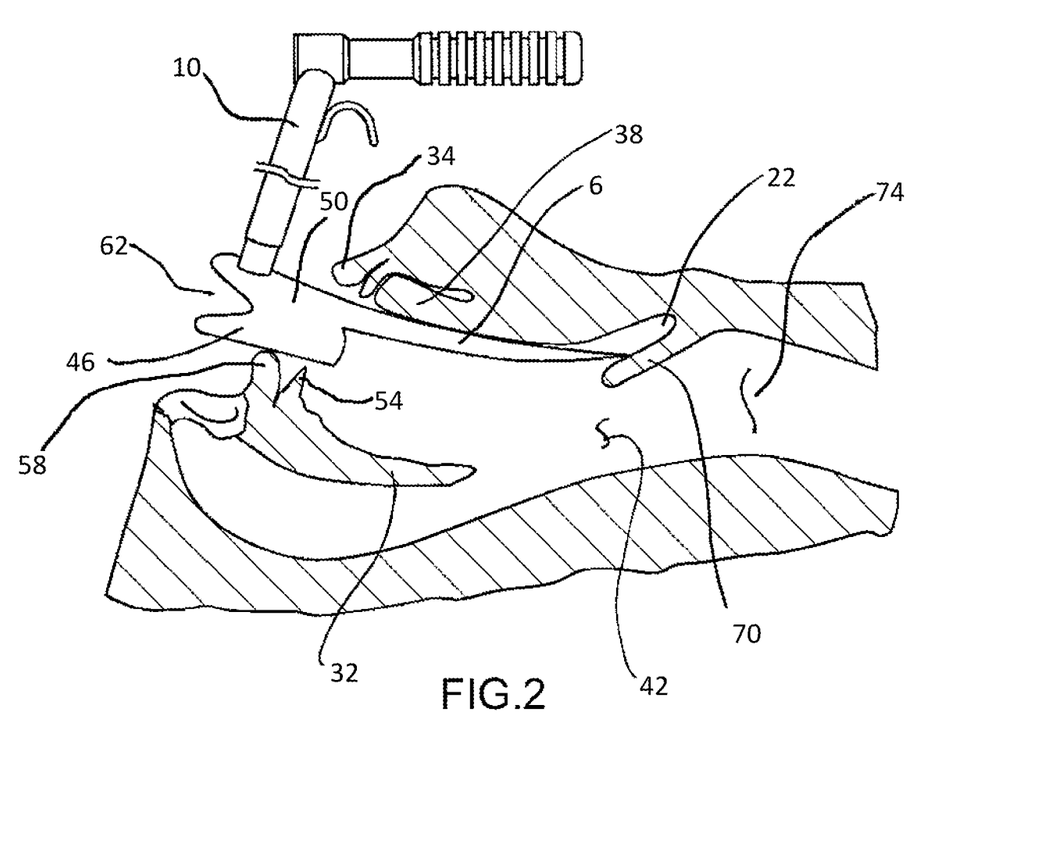
FIG. 2 is a detailed view of FIG. 1.
Figure 3:
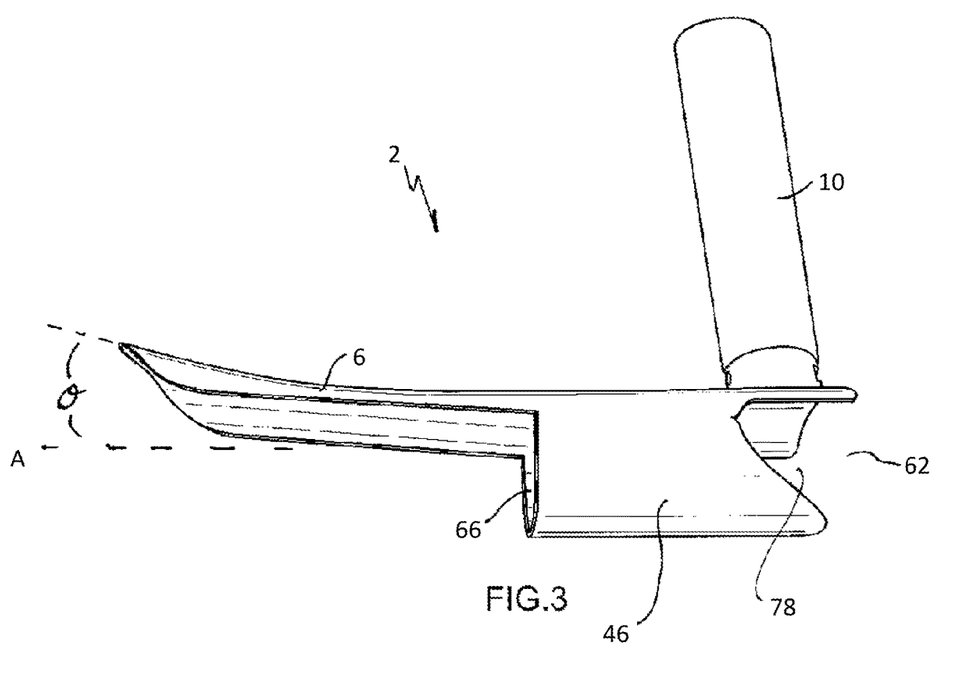
FIG. 3 is a front perspective view of the retractor of one embodiment of the present invention.
Figure 4:
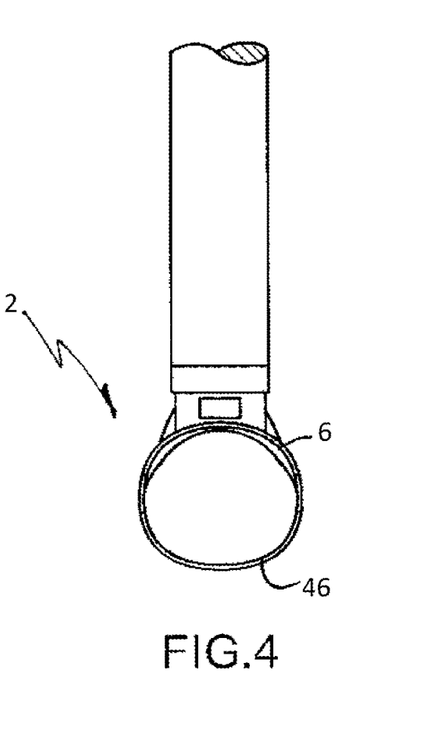
FIG. 4 is a left elevation view of FIG. 3.
Figure 5:
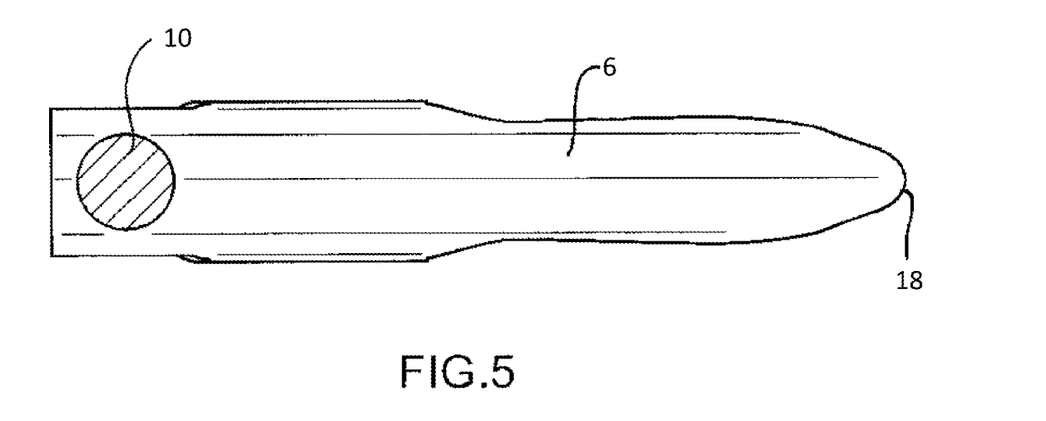
FIG. 5 is a top elevation view of FIG. 3.
Figure 6:
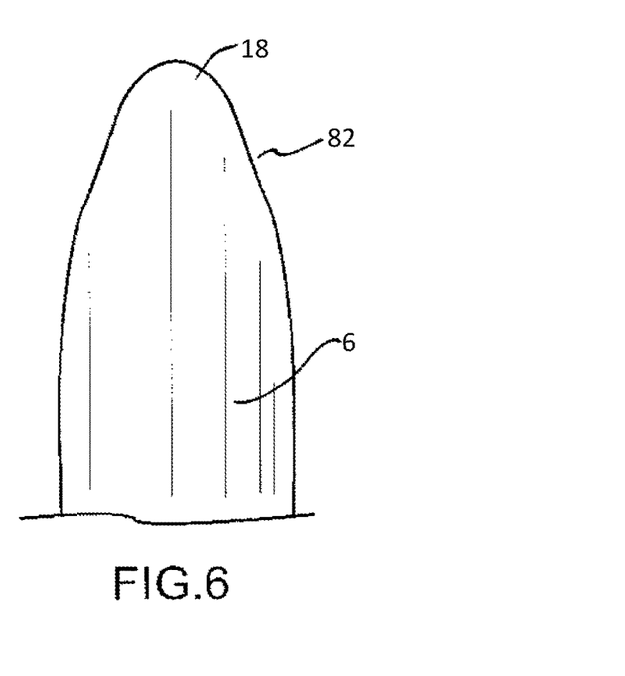
FIG. 6 is a detailed view of FIG. 5.
Figure 7:
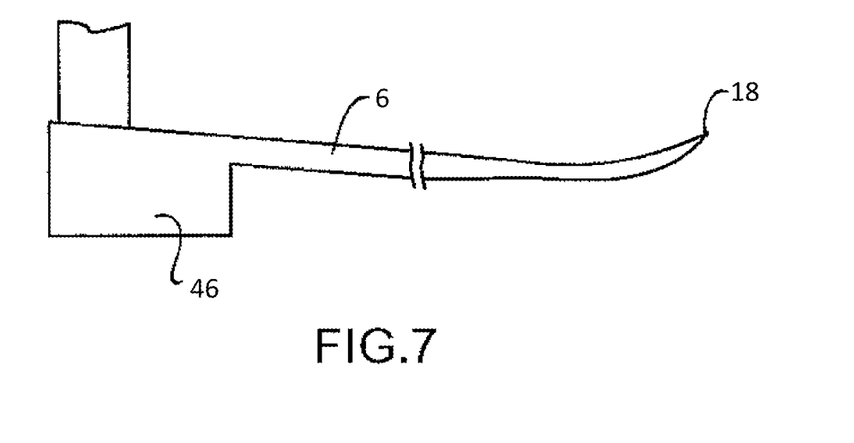
FIG. 7 is a front elevation view of a retractor of one embodiment of the present invention.
Figure 8:
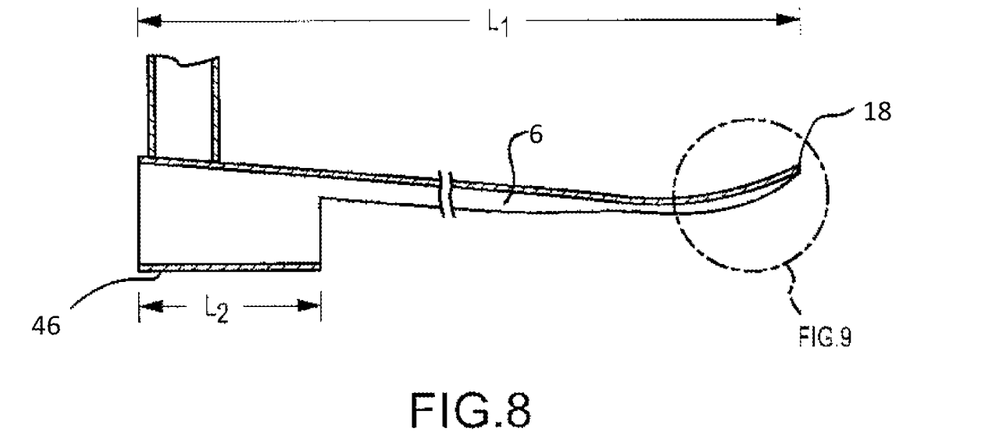
FIG. 8 is a cross-sectional view of FIG. 7.
Figure 9:
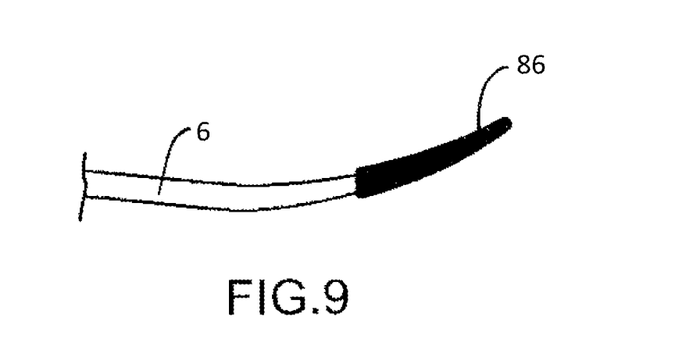
FIG. 9 is a detail view of a retractor of one embodiment of the present invention with interconnected tip extender.
Figure 10:
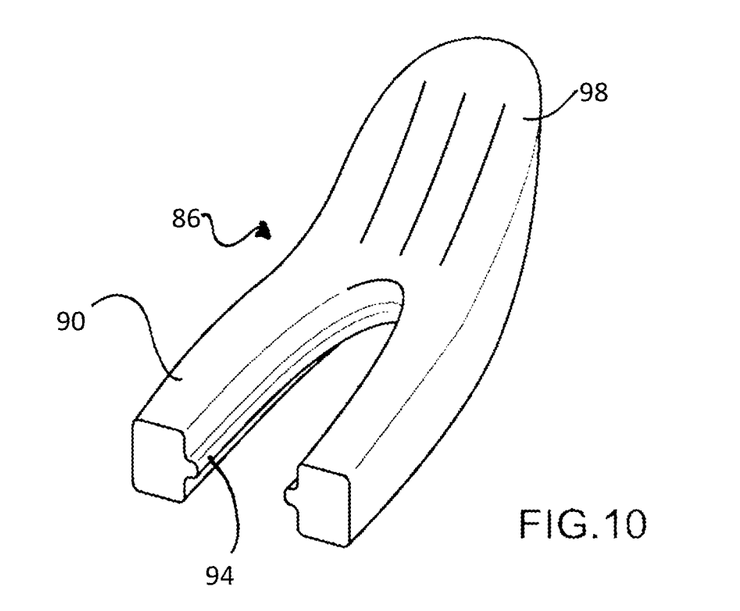
FIG. 10 is a perspective view of a tip extender of one embodiment of the present invention.
Figure 11:
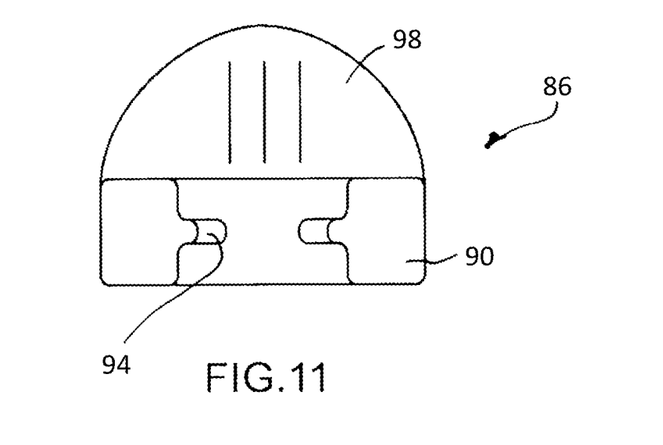
FIG. 11 is a left elevation view of the tip extender shown in FIG. 10.

To further enhance robotic surgeries, some embodiments of the present invention provide a maxilla portion that has at least one side opening 78 to accommodate lateral (e.g. side-to-side) motion of modern surgical tools. The side opening(s) may also be used to accommodate accessory instruments such as a suction catheter, clamp, or suturing tool to be passed through the maxilla portion 46 into the oral cavity. Those of ordinary skill in the art will appreciate that some robotic tools and surgical procedures do not require a side opening and, thus, this feature may be omitted. In addition, as shown in FIGS. 5 and 6, the tip of one embodiment of the present invention is tapered 82, which facilitates the use of some robotic surgical instruments.

FIGS. 9-26 show a tip extender 86 configured to interconnect to an existing blade tip that allows the surgeon to lift the patient's epiglottis, which provides enhanced visualization access to the patient's larynx, posterior arytenoid area, trachea, etc.

FIGS. 10-15 show the general concepts contemplated by one embodiment of the present invention that employs a selectively interconnected tip extender 86 adapted to mate with at least one of the blade and blade tip of existing laryngoscope retractors. The tip extender 86 shown in FIG. 10 includes a pair of legs 90 that possess and inwardly-disposed rail 94. Connecting the legs 90 is a shaped end 98 that effectively increases the length of the blade and its tip curvature, which allows the surgeon to restrain the patient's epiglottis or other desired anatomical structures. The rail 94 of each leg 90 is configured to interface with a lateral surface 102/groove 106 provided on each side of the blade. Accordingly, the tip extender 86 is prevented from rotating when secured to the blade about the blade's longitudinal axis.

Figures 12, 13:
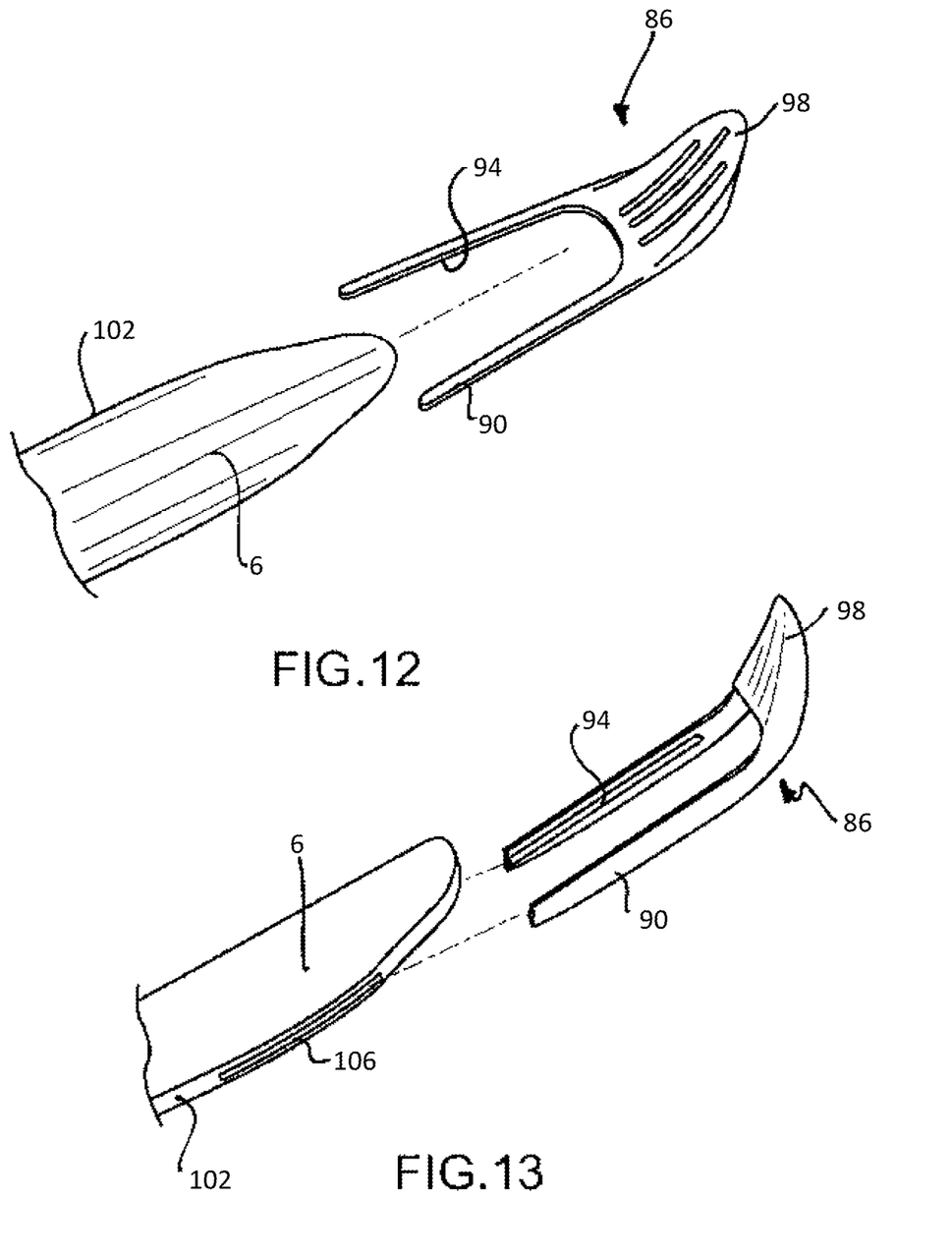
FIG. 12 is a partial top perspective view showing the tip extender of FIG. 9 configured to interconnect to a retractor blade.
FIG. 13 is a partial front perspective view showing the tip extender of FIG. 9 configured to interconnect to retractor blade.
Figure 14:
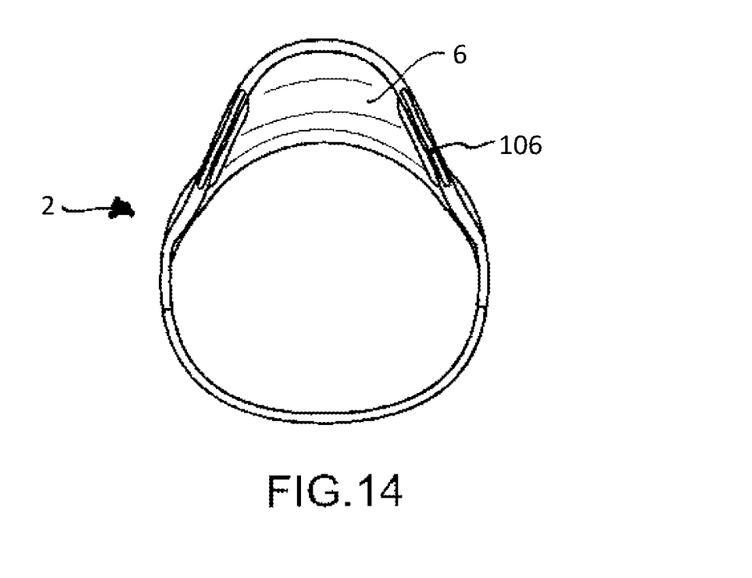
FIG. 14 is a right elevation view of a retractor adapted to selectively receive the tip extender shown in FIG. 9.

The legs of one embodiment of the present invention are biased inwardly, wherein interconnecting the tip extender 86 to the blade will flex the legs 90 outwardly, thereby creating an interference fit between the two components that effectively secures the tip extender 86 to the blade. As shown in FIGS. 13 and 14, the rails 94 are selectively received by corresponding grooves 106 or slots integrated into the blade's lateral surface 102. This feature contemplates a single use such that after the procedure the tip extender 86 is removed from the blade 6 and discarded. The tip extender 86 may alternatively be made of plastic, metal, or comparable material that can be sterilized and reused. Other embodiments of the present invention provide a more permanent retrofit by mechanically securing the tip extender to the blade by welds, bonding agents, set screws, etc.

Figure 15:
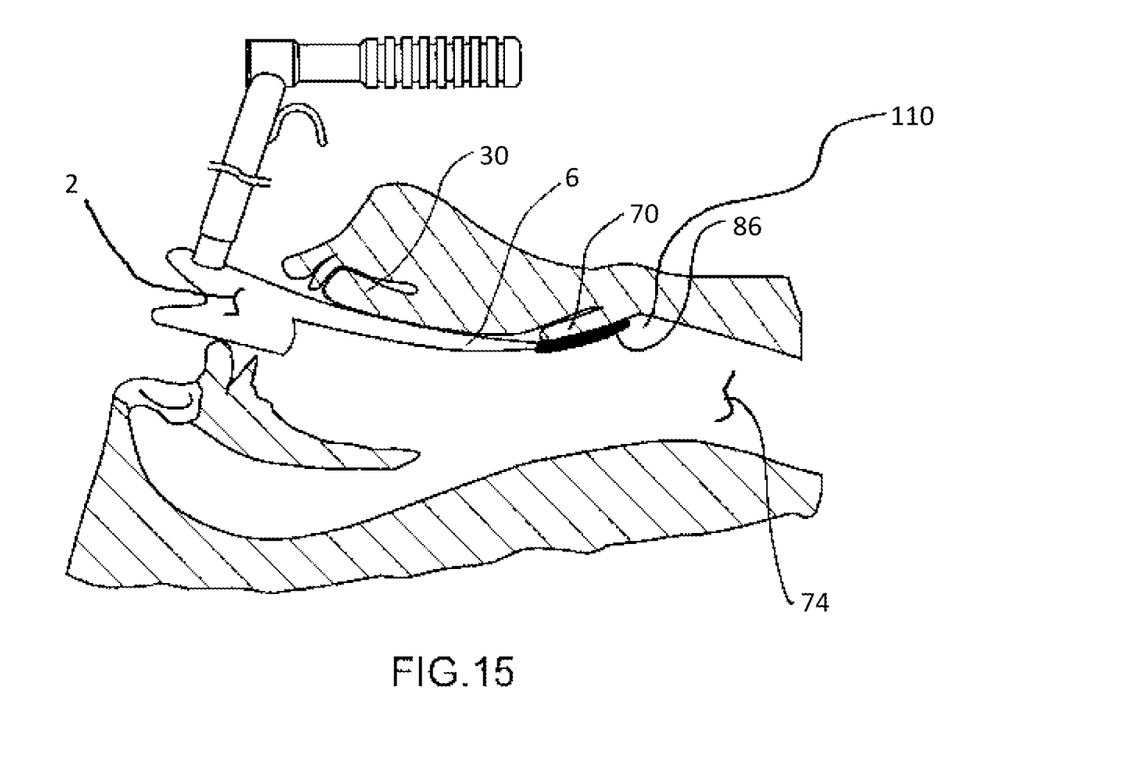
FIG. 15 is an elevation view of the retractor that employs a tip extender of one embodiment of the present invention positioned in a patient's mouth.

FIG. 15 shows a retractor blade 6 with interconnected tip extender 86 that lifts the epiglottis 70 for enhanced visualization of the laryngeal introitus. As one of ordinary skill will appreciate, the tip extender 86, which has an end configured to rest near the patient's epiglottic petiole 110, provides an enhanced degree of lift. Here, the patient's tongue 30, epiglottis 70, and anterior commisure are restrained to provide a clear view of the patient's false vocal folds, true vocal folds 74, glottis, and deep into the patient's glottis and trachea.

Figures 16, 17:
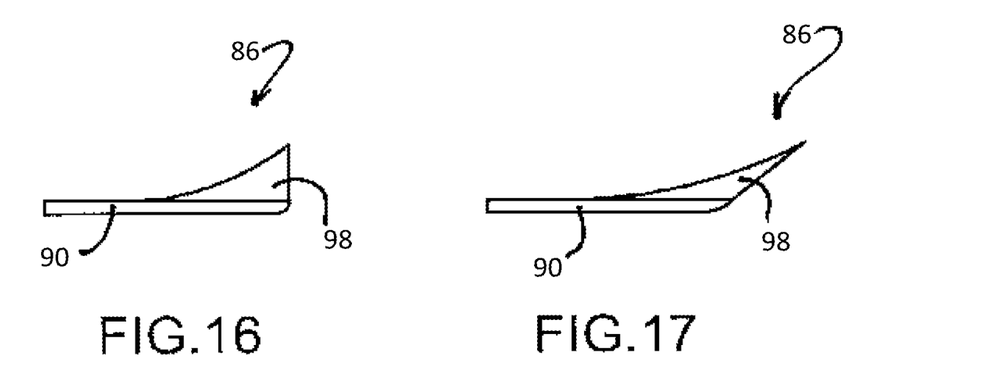
FIG. 16 is a front elevation view of a tip extender employing a triangular end profile.
FIG. 17 is a front elevation view of a tip extender employing a triangular end profile.
Figure 18:
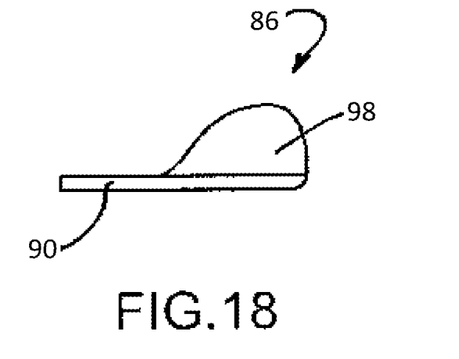
FIG. 18 is a front elevation view of a tip extender employing a bulbous end profile.
Figure 19:
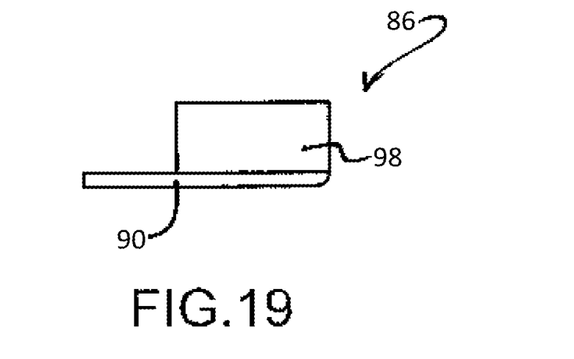
FIG. 19 is a front elevation view of a tip extender employing a square or rectangular and profile.

FIGS. 16-19 show different tip extender end configurations contemplated by some embodiments of the present invention. Those of ordinary skill in the art will appreciate that many more tip configurations may be used to accommodate a wide variety of patients. FIGS. 16 and 17 comprise triangular-shaped ends. FIG. 18 comprises a tip extender 86 with a bulbous end and FIG. 19 provides a tip extender with a rectangular-shaped end. Again, the end can be of any shape and maybe moldable and set to a final form prior to surgery. Furthermore, some ends comprise removable portions that allow the surgeon to selectively modify tip shape. The end may include lights, a recording device, a probe, a medicine delivery means, a camera, etc. to help the surgeon visually appreciate and treat a given portion of the patient's anatomy.

Figure 20:
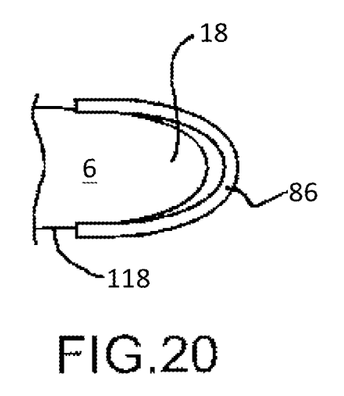
FIG. 20 is a top elevation view of a tip extender of another embodiment of the present invention interconnected to a laryngoscope blade.
Figure 21:
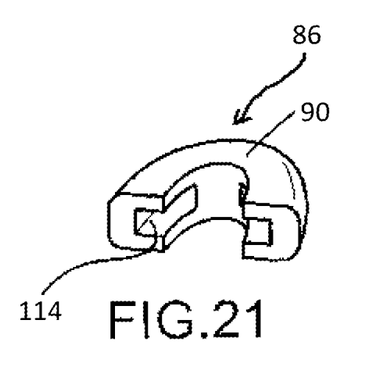
FIG. 21 is a perspective view of the tip extender shown in FIG. 20.
Figure 22:
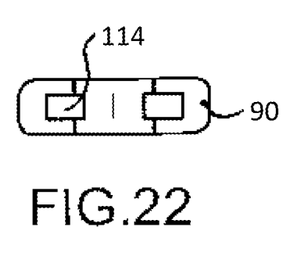
FIG. 22 is a left elevation view of the tip extender shown in FIG. 20.

FIGS. 20-22 show a simplified, horseshoe-shaped tip extender 86 of another embodiment of the present invention. The tip extender 80 employs legs 90 that selectively engage the lateral surface or edge of a laryngoscope blade and can include a rail as described above. More commonly, however, this embodiment comprises an internally-disposed track 114 that receives the lateral edge of a blade. The legs 90 of the tip extender 86 may be biased inwardly as described above to provide an interference fit between the tip extender and the blade. Alternatively, the track 114 or inner surface of the tip extender 86 may comprise a compliant surface that helps grip the lateral surface or lateral edge 118 of the blade 6. If a permanent interconnection is desired, the tip extender 86 can be welded, bonded, or otherwise interconnected to the blade as described above.

Figure 23:
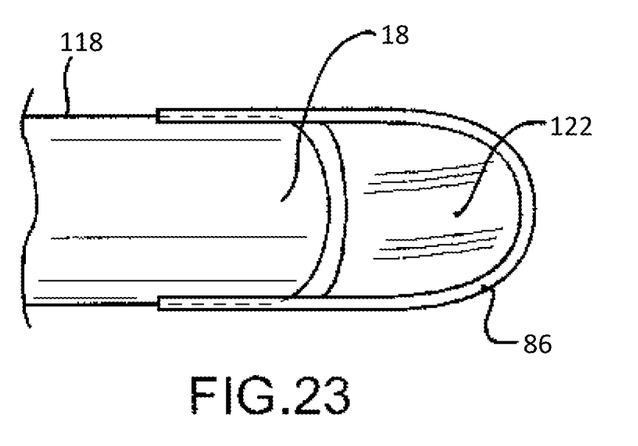
FIG. 23 is a top elevation view of a tip extender of another embodiment of the present invention similar to that shown in FIG. 20 interconnected to a laryngoscope blade.

FIG. 23 shows a tip extender of yet another embodiment of the present invention somewhat similar to that shown in FIGS. 21-22, but which includes a floor 122 provided between the legs. The floor acts as a spoon to facilitate holding the epiglottis. In addition, the floor may be used to accommodate tip ends as shown in FIG. 16-19. In some embodiments of the present invention, the floor is used to accommodate a moldable tip end.

Figure 24:
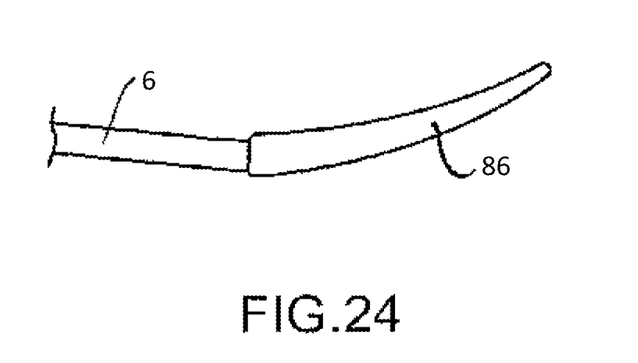
FIG. 24 is a front elevation view of a tip extender of another embodiment of the present invention interconnected to a laryngoscope blade.
Figure 25:
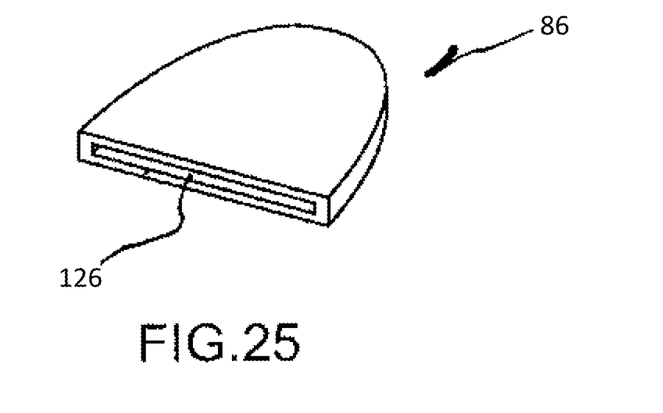
FIG. 25 is a perspective view of the tip extender shown in FIG. 24.
Figure 26:
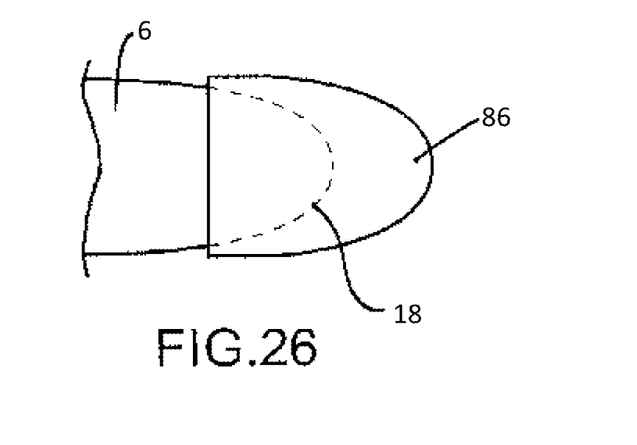
FIG. 26 is a top elevation view of the tip extender shown in FIG. 24 interconnected to a laryngoscope blade.

FIGS. 24-26 show yet another embodiment of the present invention. Here, the tip extender 86 includes a cavity 126 adapted selectively receive the tip 6 of a laryngoscope retractor blade 6. The tip extender 86 may be secured to the blade 6 in any of the ways discussed herein.

While various embodiments of the present invention have been described in detail, it is apparent that modifications and alterations of those embodiments will occur to those skilled in the art. It is to be expressly understood that such modifications and alterations are within the scope and spirit of the present invention, as set forth in the following claims. Further, it is to be understood that the invention(s) described herein is not limited in its application to the details of construction and the arrangement of components set forth in the preceding description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. A retractor adapted for use with a laryngoscope, comprising:
   a blade having a proximal end and a distal end;
   a maxilla portion interconnected to the blade, wherein the maxilla portion and the blade are curved about a longitudinal axis of the retractor that generally corresponds to a length of the blade to provide at least a portion of a passage adapted to selectively receive a medical instrument, wherein the maxilla portion has a proximal end and a distal end that define a length that is less than or equal to 75% of the length of the blade;
   a tip extender interconnected to the distal end of the blade;
   wherein the proximal end and the distal end define a first length with lateral edges, the blade being adapted to constrain at least a portion of a patient's tongue;
   wherein the maxilla portion has a proximal end and a distal end that is spaced from the proximal end of the blade; and
   wherein the distal end of the maxilla portion is closer to the proximal end of the blade than the distal end of the blade, such that a majority of the blade is exposed.

2. The retractor of claim 1, wherein the tip extender has an opening associated with a cavity that receives the distal end of the blade.

3. The retractor of claim 1, wherein the tip extender has a tip with a triangular profile or a bulbous profile.

4. The retractor of claim 1, wherein the tip extender has a tip with a selectively deformable portion.

5. The retractor of claim 1, wherein the tip extender is comprised of a curved tip portion with a first leg and a second leg extending therefrom.

6. The retractor of claim 1, wherein the maxilla portion has a first lateral edge and a second lateral edge interconnected to the lateral edges of the blade, wherein a proximal end of the first lateral edge and a proximal end of the second lateral edge are spaced from the proximal end of the blade, wherein the maxilla portion comprises a curved surface that extends from the first lateral edge to the second lateral edge, and wherein the curved surface includes an outer portion with a longitudinal dimension greater than a length of the first lateral edge and a length of the second lateral edge, the outer portion having a proximal end that generally corresponds with the proximal end of the blade.

7. The retractor of claim 6, wherein the proximal end of the maxilla portion provides a lateral opening in the retractor.

8. A retractor, comprising:
   a first member having a proximal end and a distal end;
   a second member interconnected to the first member, wherein at least one of the first member and the second member are curved about a longitudinal axis of the retractor that generally corresponds to a length of the first member to provide a passage;
   wherein the second member has a length that is substantially less than that of the first member;
   a tip extender interconnected to the distal end of the first member;
   wherein the proximal end and the distal end defines a first length with lateral edges,
   wherein the second member has a proximal end and a distal end that is spaced from the proximal end of the blade, the first member and the second member defining a passage with a longitudinal axis; and
   wherein the distal end of the second member is closer to the proximal end of the blade than the distal end of the blade.

9. The retractor of claim 8, wherein the tip extender has an opening associated with a cavity that receives the distal end of the first member.

10. The retractor of claim 8, wherein the tip extender has a tip with a triangular profile or a bulbous profile.

11. The retractor of claim 8, wherein the tip extender has a tip with a selectively deformable portion.

12. The retractor of claim 8, wherein the tip extender is comprised of a curved tip portion with a first leg and a second leg extending therefrom.

13. The retractor of claim 8, wherein the second portion is selectively interconnected to the first portion.

14. The retractor of claim 8, wherein the second member has a first lateral edge and a second lateral edge interconnected to the lateral edges of the first member, the second member also comprising a shaped surface that extends from the first lateral edge to the second lateral edge of the second member, and wherein the shaped surface includes an outermost extent with a longitudinal dimension greater than at least one of a length of the first lateral edge and a length of the second lateral edge.

15. The retractor of claim 14, wherein proximal ends of the first lateral edge and the second lateral edge are spaced from the proximal end of the first member to define at least one lateral opening in the retractor.

16. A retractor adapted for use with a laryngoscope, comprising:
    a blade having a proximal end and a distal end;
    a maxilla portion interconnected to the blade, wherein the maxilla portion and the blade are curved about a longitudinal axis of the retractor that generally corresponds to a length of the blade to provide a passage configured to selectively receive a medical instrument;
    wherein the maxilla portion has proximal end and a distal end that define a length that is substantially less than the length of the blade;
    wherein the distal end of the blade has a tapered shape;
    wherein the maxilla portion has a first lateral edge and a second lateral edge interconnected to corresponding lateral edges of the blade, the maxilla portion further comprised of a shaped surface that extends from the first lateral edge to the second lateral edge, the shaped surface including an outer portion with a longitudinal dimension greater than a length of the first lateral edge and the second lateral edge;
    wherein the proximal end of the maxilla portion provides a lateral opening in the retractor;
    wherein the distal end of the blade is spaced transversely from the longitudinal axis of the retractor;
    a tip extender interconnected to the distal end of the blade;
    wherein proximal ends of the first and second lateral edges are spaced from the proximal end of the blade; and
    wherein the distal end of the maxilla portion is closer to the proximal end of the blade than the distal end of the blade.

17. The retractor of claim 16, wherein the tip extender has a tip with a selectively deformable portion.

* * * * *